(12) United States Patent
Ono et al.

(10) Patent No.: US 6,180,396 B1
(45) Date of Patent: Jan. 30, 2001

(54) CARBON PRODUCING APPARATUS UTILIZING BIOMASS

(75) Inventors: Shigeki Ono, Kyoto; Saburo Kato, Shiga, both of (JP)

(73) Assignees: Research Institute of Innovative Technology for the Earth; Shimadzu Corporation, both of Kyoto (JP)

( * ) Notice: Under 35 U.S.C. 154(b), the term of this patent shall be extended for 0 days.

(21) Appl. No.: 09/264,671

(22) Filed: Mar. 9, 1999

(30) Foreign Application Priority Data

Mar. 13, 1998 (JP) .................................................. 10-082670
Dec. 25, 1998 (JP) .................................................. 10-370016

(51) Int. Cl.[7] .................................................. C12M 1/107
(52) U.S. Cl. .................................. 435/289.1; 435/300.1; 422/150
(58) Field of Search ............................ 435/289.1, 290.1, 435/300.1, 801; 71/10; 210/603; 422/150, 158; 423/220, 230, 231, 449.1, 450, 453, 454, 458; 48/127.3, 127.5, 127.7, 198.1

(56) References Cited

U.S. PATENT DOCUMENTS

| | | | |
|---|---|---|---|
| 1,852,497 | * | 4/1932 | Woodhouse . |
| 3,383,309 | * | 5/1968 | Chandler . |
| 3,771,959 | * | 11/1973 | Fletcher et al. . |
| 4,289,625 | * | 9/1981 | Tarman et al. . |
| 4,394,136 | | 7/1983 | Grabis . |
| 4,798,801 | | 1/1989 | Hitzman . |
| 4,836,898 | * | 6/1989 | Noyes . |
| 5,093,303 | * | 3/1992 | Tamaura . |
| 5,316,750 | * | 5/1994 | Szegu et al. . |
| 5,513,494 | * | 5/1996 | Flynn et al. . |
| 5,580,457 | * | 12/1996 | Erickson . |

FOREIGN PATENT DOCUMENTS

| | | | |
|---|---|---|---|
| 196 49 244 A1 | | 5/1998 | (DE) . |
| 0 890 388 | * | 1/1999 | (EP) . |
| 4-235738 | * | 8/1992 | (JP) . |
| 11-029314 | * | 2/1999 | (JP) . |

OTHER PUBLICATIONS

KREIS. CAPLUS Abstract No. 1980:25423 of USEPA, Office of Res. Dev. EPA (1979), EPA–600/2–79–142, 59pp.*
Chemical Abstracts, vol. 88, No. 5, Jan. 30, 1978; Columbus, Ohio, U.S.; abstract No. 34362, Bekes, J. et al: "Decomposition of methanol under the conditions of anaerobic fermentation" XP002106179.
Database WPI; Section Ch, Week 9431; Derwent Publications Ltd., London, GB; XP002106180 & RU 2 005 789 C (Argric Electrif Res Inst) Jan. 15, 1994.

* cited by examiner

*Primary Examiner*—William H. Beisner
(74) *Attorney, Agent, or Firm*—Armstrong, Westerman, Hattori, McLeland & Naughton

(57) ABSTRACT

An anaerobic fermentation part generates gas containing methane and carbon dioxide by anaerobically fermenting biomass. The gas is passed to a methane.carbon dioxide separation part to be separated into methane and carbon dioxide, and part of the separated methane is fed to a methane reforming part to be decomposed into carbon and hydrogen under the presence of a catalyst. The carbon dioxide separated in the methane.carbon dioxide separation part and the hydrogen formed in the methane reforming part are fed to a carbon dioxide fixing part, which in turn reacts the carbon dioxide with the hydrogen under the presence of a catalyst for continuously forming carbon and hydrogen and fixing the carbon dioxide.

19 Claims, 10 Drawing Sheets

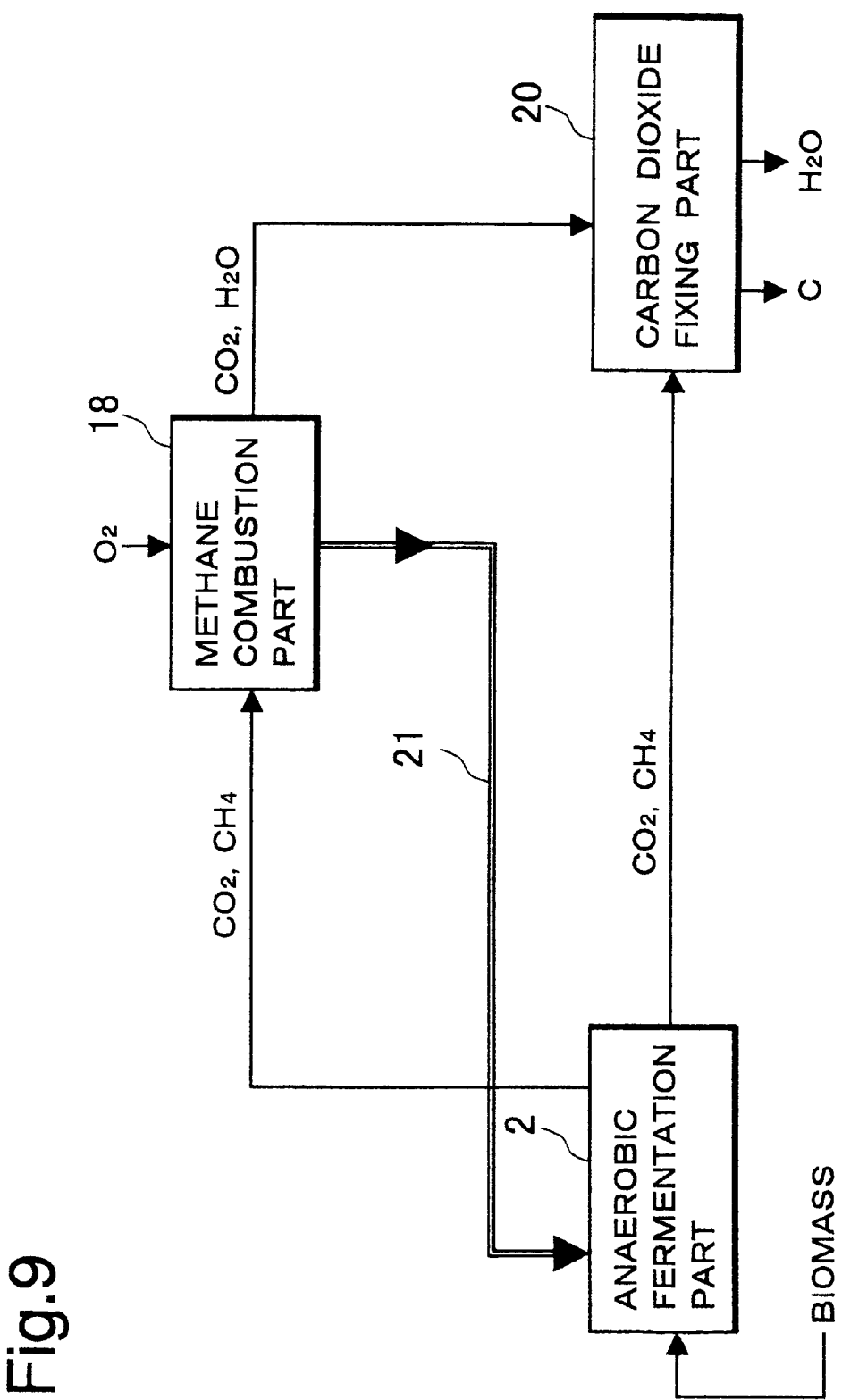

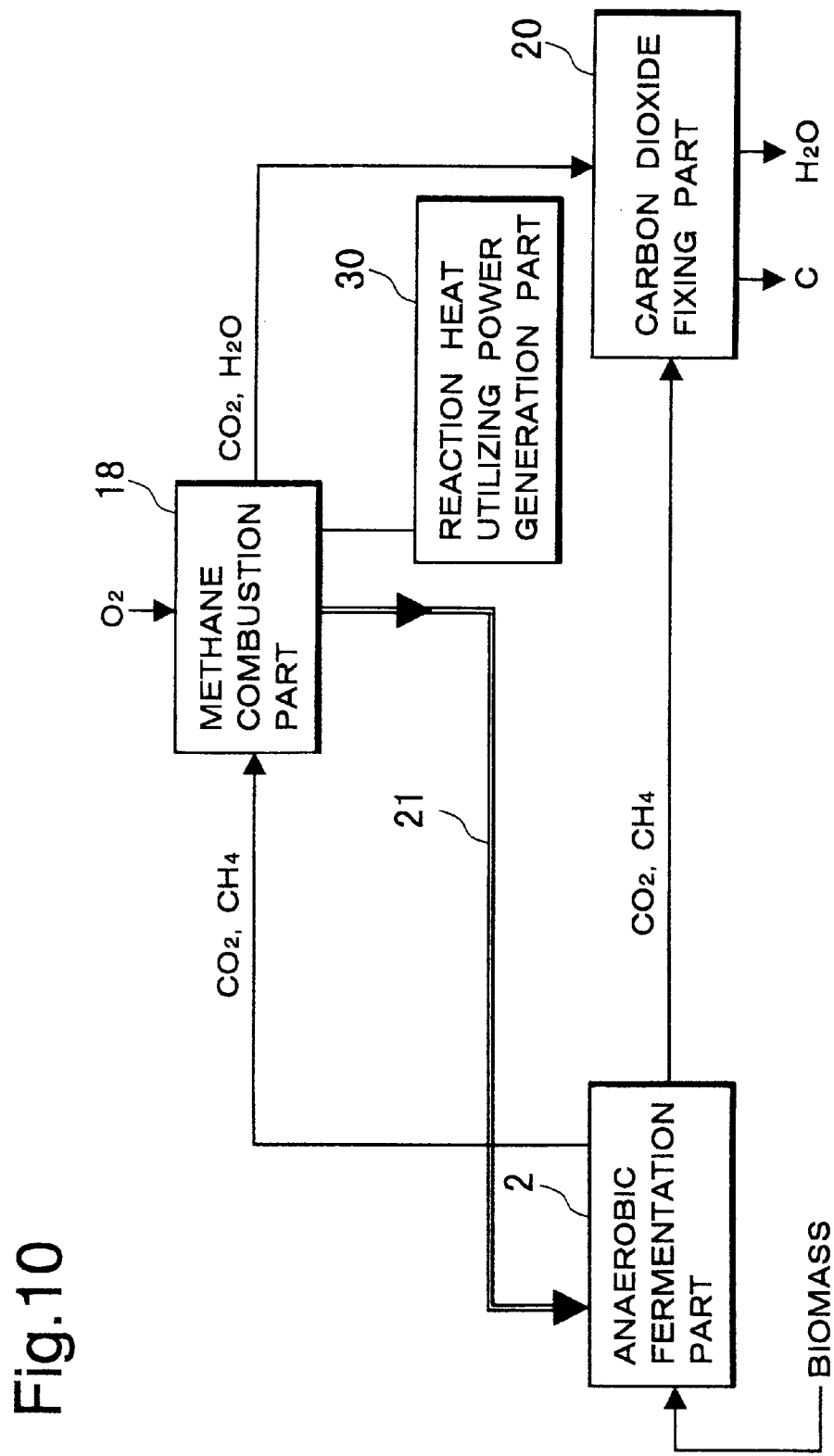

CARBON PRODUCING APPARATUS UTILIZING BIOMASS

BACKGROUND OF THE INVENTION

1. Field of the Invention

The present invention relates to the field of environmental control concerning sewage treatment, stack gas desulfurization, garbage treatment and livestock waste disposal as well as the fields of carbon black production, methanol production, dimethyl ether production and gasoline production.

2. Description of the Prior Art

According to estimated data related to the carbon cycle by the intergovernmental panel on climatic change (IPCC), artificially discharged carbon dioxide ($CO_2$) amounts to about 71 hundred million tons a year in terms of carbon. It is considered that about half remains in the atmosphere while the other half is absorbed by the sea and others. Carbon dioxide, known as greenhouse effect gas, is regarded as a cause for global warming.

In order to reduce the concentration of carbon dioxide in the atmosphere, it is indispensable to suppress the discharge thereof itself. Various methods are studied for reducing the discharge of carbon dioxide.

A method of reducing carbon dioxide under a hydrogen ($H_2$) atmosphere and converting the same to pulverized carbon has been devised in order to fix carbon dioxide contained in the atmosphere or discharged in great volume from power plants, steelworks, or heavy and chemical plants on the discharge source, and recycle the same. The conversion system therefore is formed by a carbon dioxide separator for separating carbon dioxide from the atmosphere or exhaust gas, a carbon dioxide concentrator for concentrating the separated carbon dioxide, a $CO_2/H_2$ reactor for forming pulverized carbon by reacting the carbon dioxide with hydrogen under the presence of a catalyst and the like.

While electrolysis of water, solar battery power generation, utilization of hydrogen absorbing alloys or the like has been proposed as a method of obtaining hydrogen necessary for converting carbon dioxide to pulverized carbon and fixing the same, a carbon dioxide fixing apparatus has not yet been put into practice since hydrogen is extremely costly.

SUMMARY OF THE INVENTION

The objective of the present invention is to provide an apparatus which can fix carbon dioxide at a low cost An apparatus according to an aspect of the present invention comprises an anaerobic fermentation part for anaerobically fermenting biomass and generating methane and carbon dioxide, a methane.carbon dioxide separation part for separating methane and carbon dioxide from mixed gas containing methane and carbon dioxide generated in the anaerobic fermentation part, hydrogen forming means for forming hydrogen from the methane separated in the methane.carbon dioxide separation part, and a carbon dioxide fixing part for forming carbon by reducing the carbon dioxide separated in the methane.carbon dioxide separation part under the presence of a catalyst with the hydrogen formed in the hydrogen forming means.

An example of the hydrogen forming means is a methane reforming part for decomposing methane into carbon and hydrogen under the presence of a catalyst, and another example is a methane steam reforming part for forming carbon dioxide and hydrogen by reacting methane with steam under the presence of a catalyst An apparatus according to another aspect of the present invention comprises the anaerobic fermentation part and a carbon dioxide fixing part receiving mixed gas containing methane and carbon dioxide formed in the anaerobic fermentation part and reacting the same under the presence of a catalyst for forming carbon.

The carbon dioxide fixing part reduces the carbon dioxide with hydrogen under the presence of the catalyst for forming crystalline pulverized carbon. The hydrogen results from methane obtained by anaerobically fermenting biomass.

The apparatus according to the present invention comprises the anaerobic fermentation part for forming methane and carbon dioxide by anaerobically fermenting biomass and decomposes the methane formed in the anaerobic fermentation part into carbon and hydrogen with the catalyst or forms carbon dioxide and hydrogen by reacting the methane formed in the anaerobic fermentation part with steam under the presence of the catalyst, thereby obtaining hydrogen occupying at least 90% of the energy for fixing the carbon dioxide, whereby hydrogen can be obtained at a low cost for reducing the cost of fixing the carbon dioxide.

The anaerobic fermentation part must be heated to a prescribed temperature. Energy is necessary for the remaining part having endothermic reaction. If at least part of the necessary energy can be ensured in the system, the cost can be reduced. Therefore, it is preferable to utilize combustion heat generated by combusting methane by providing a methane combustion part for combusting part of the methane generated in the anaerobic fermentation part, or generated by combusting hydrogen by providing a hydrogen combustion part for combusting part of the hydrogen formed in the system. If any part other than the methane combustion part or the hydrogen combustion part generates heat, this heat can also be utilized. Thus, it is possible to contribute to reduction of the operation cost if the necessary heat can be generated in the system.

If the combustion heat generated by combusting methane or hydrogen is still left after being utilized for heating the remaining part, the residual heat can be utilized for a part of electric power for operating the apparatus by providing a reaction heat utilizing power generation part for converting the heat to electric power, thereby contributing to reduction of the operation cost also at this point When providing the methane combustion part, it is preferable to lead carbon dioxide generated by combusting methane to the carbon dioxide fixing part for fixing the same as carbon. Mixed gas containing steam and carbon dioxide generated from the methane combustion part may be directly led to the carbon dioxide fixing part, or carbon dioxide separated by a vapor-liquid separator may be supplied to the carbon dioxide fixing part through an intra-system carbon dioxide supply part formed by a steam condenser and the vapor-liquid separator.

When providing the methane combustion part, it is preferable to adjust the ratio of the gas generated in the anaerobic fermentation part fed to the carbon dioxide fixing part, to that fed to the methane combustion part so that the sum of the mole numbers of the carbon dioxide fed from the methane combustion part to the carbon dioxide fixing part, and that fed from the anaerobic fermentation part to the carbon dioxide fixing part is equal to the mole number of the methane fed to the carbon dioxide fixing part. Thus, all carbon dioxide formed in the system of the apparatus can be fixed.

The carbon dioxide fixing part can also be supplied with carbon dioxide from outside the system.

The foregoing along with other objects, features, aspects and advantages of the present invention will become more apparent from the following detailed description of the present invention when taken in conjunction with the accompanying drawings.

BRIEF DESCRIPTION OF THE DRAWINGS

FIG. 9 is a block diagram showing a ninth embodiment of the present invention; and FIG. 10 is a block diagram showing a tenth embodiment of the present invention.

DESCRIPTION OF THE PREFERRED EMBODIMENTS

Figure 1:
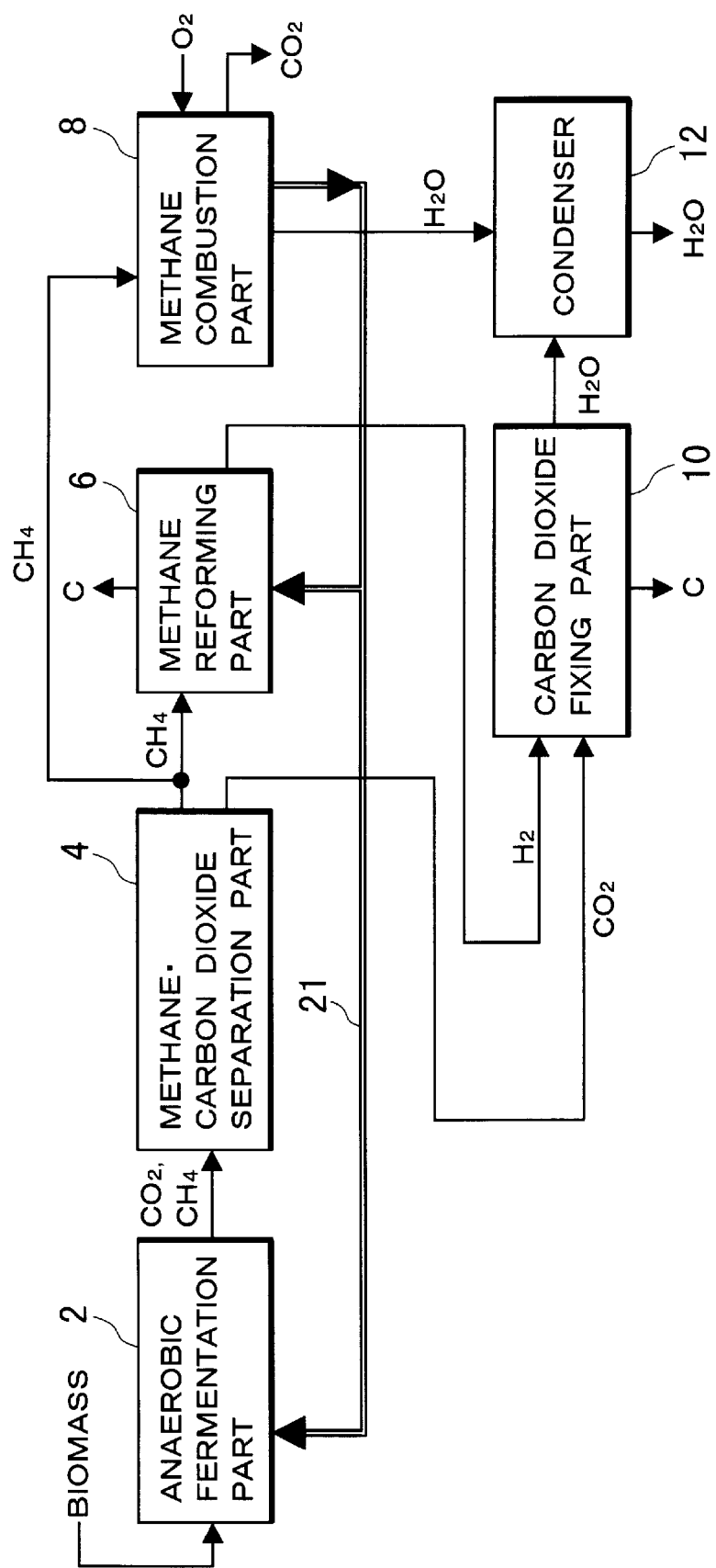
FIG. 1 is a block diagram showing a first embodiment of the present invention.

FIG. 1 is a block diagram showing the first embodiment of the present invention.

An anaerobic fermentation part 2 is provided for obtaining methane and carbon dioxide by decomposing organic waste such as paper, beer waste, beer lees or kitchen garbage with bacteria in an anaerobic fermenter. The anaerobic fermentation part 2 is connected to a methane.carbon dioxide separation part 4, which comprises an adsorbent such as zeolite for separating gas generated in the anaerobic fermentation part 2 into methane and carbon dioxide through adsorbing and desorbing functions of the adsorbent.

The methane.carbon dioxide separation part 4 is connected to a methane reforming part 6 and a methane combustion part 8. The methane reforming part 6 which comprises a catalyst such as Ni or Co with a carrier of $SiO_2$ or $Al_2O_3$, for example, is supplied with part of the methane separated in the methane.carbon dioxide separation part 4, and decomposes the methane into carbon and hydrogen under heating at 400 to 900° C., e.g., 530° C.

The methane combustion part 8 combusts part of the methane separated in the methane.carbon dioxide separation part 4, and supplies the resulting combustion heat to the anaerobic fermentation part 2 and the methane reforming part 6 through a reaction heat transmission part 21 such as a heat exchanger or a heat transmission path.

In order to reduce the carbon dioxide separated in the methane.carbon dioxide separation part 4 with hydrogen and fixing the same as carbon, a carbon dioxide fixing part 10 is connected to the methane.carbon dioxide separation part 4 and the methane reforming part 6. The carbon dioxide fixing part 10 comprises a catalyst such as Ni or Co with a carrier of $SiO_2$ or $Al_2O_3$, for example, and reduces the carbon dioxide separated in the methane.carbon dioxide separation part 4 with hydrogen generated in the methane reforming part 6 under heating at 400 to 900° C. for forming pulverized carbon. Carbon dioxide generated in the methane combustion part 8 can also be led to the carbon dioxide fixing part 10 through a passage, to be converted to carbon and fixed.

A condenser 12 is provided for condensing steam ($H_2O$) formed in the carbon dioxide fixing part 10 and that formed in the methane combustion part 8.

The operation of the first embodiment shown in FIG. 1 is now described as follows:

When biomass is introduced into an anaerobic fermenter of the anaerobic fermentation part 2 storing methane bacteria, gas containing methane and carbon dioxide is generated due to anaerobic fermentation of the biomass. The gas is passed to the methane.carbon dioxide separation part 4, to be separated into methane and carbon dioxide. The methane reforming part 6 decomposes part of the methane into carbon (C) and hydrogen under the presence of a catalyst. The carbon is precipitated as crystalline pulverized solid carbon in the methane reforming part 6. The thermochemical equation for the reaction in the methane reforming part 6 is as follows:

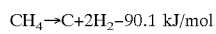
$$CH_4 \rightarrow C + 2H_2 - 90.1 \text{ kJ/mol}$$

As to the reaction heat in the thermochemical equation, symbols + and − represent the exothermic reaction and the endothermic reaction respectively. This also applies to the following thermochemical equations.

Part of the methane separated in the methane.carbon dioxide separation part 4 is also fed to the methane combustion part 8 to be combusted. The combustion heat is utilized as a heat source for the anaerobic fermentation part 2 and the methane reforming part 6. The reaction in the methane combustion part 8 is as follows:

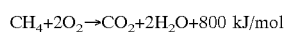
$$CH_4 + 2O_2 \rightarrow CO_2 + 2H_2O + 800 \text{ kJ/mol}$$

The carbon dioxide separated in the methane.carbon dioxide separation part 4 and the hydrogen formed in the methane reforming part 6 are fed to the carbon dioxide fixing part 10, which in turn reduces the carbon dioxide with the hydrogen under the presence of a catalyst for continuously forming carbon (C) and steam. The carbon is precipitated as crystalline pulverized solid carbon also in the carbon dioxide fixing part 10, while the steam is led to the condensation part 12 to be condensed and discharged.

The reaction in the carbon dioxide fixing part 10 is as follows:

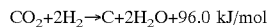
$$CO_2 + 2H_2 \rightarrow C + 2H_2O + 96.0 \text{ kJ/mol}$$

Figure 2:
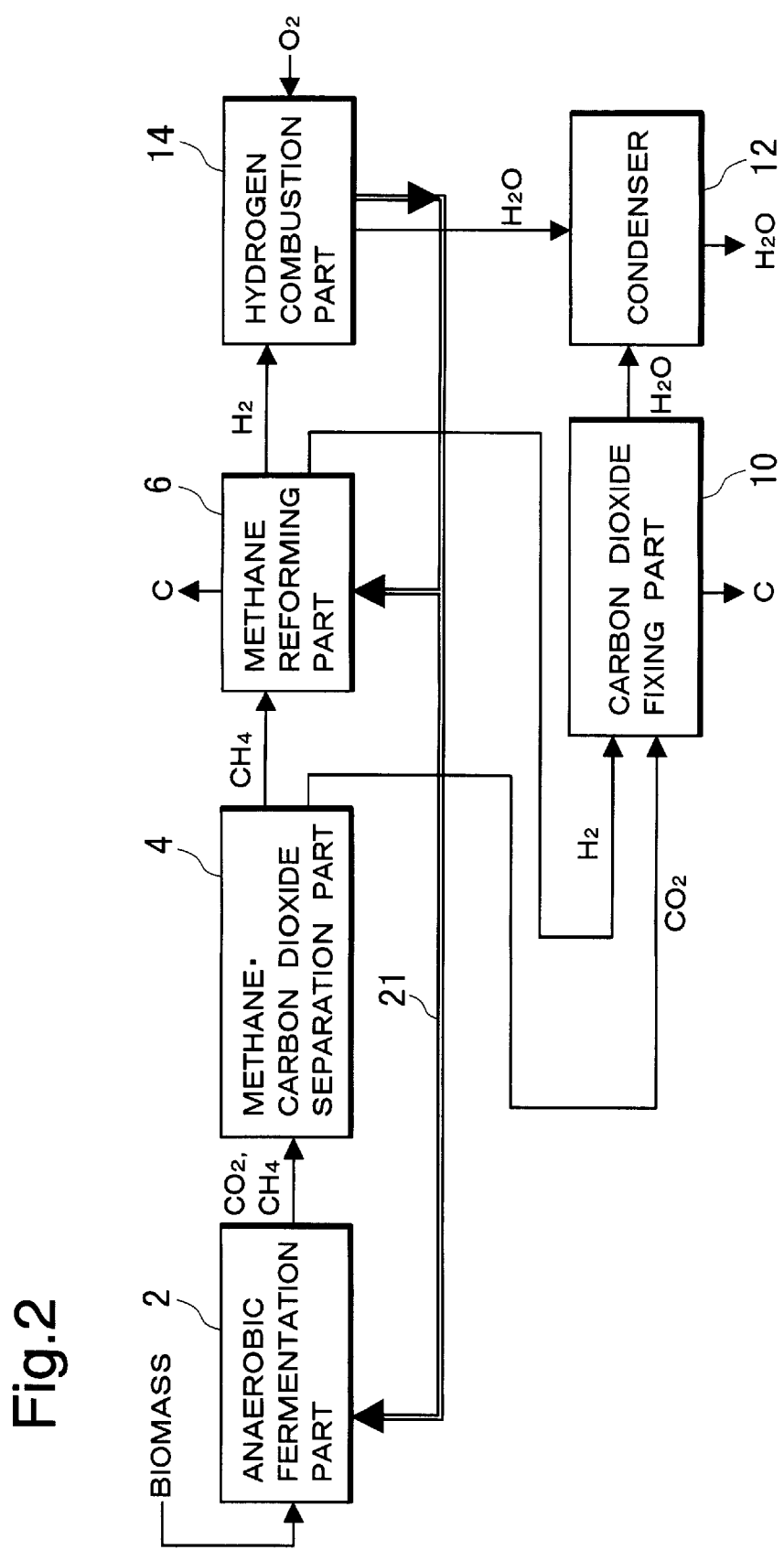
FIG. 2 is a block diagram showing a second embodiment of the present invention.

FIG. 2 is a block diagram showing the second embodiment of the present invention.

Similarly to the first embodiment shown in FIG. 1, the anaerobic fermentation part 2 is connected to the methane.carbon dioxide separation part 4, which separates gas generated in the anaerobic fermentation part 2 into methane and carbon dioxide. The methane reforming part 6 is provided for decomposing the methane separated in the methane.carbon dioxide separation part 4 into carbon and hydrogen, while the carbon dioxide fixing part 10 is connected to the methane.carbon dioxide separation part 4 for fixing the carbon dioxide separated therein with the hydrogen generated in the methane reforming part 6 and fixing the same as pulverized carbon.

The second embodiment is different from the first embodiment shown in FIG. 1 in a part for obtaining a heat source for the anaerobic fermentation part 2 and the methane reforming part 6. While the first embodiment is provided with the methane combustion part 8 for combusting part of the methane separated in the methane.carbon dioxide separation part 4, the second embodiment is provided with a hydrogen combustion part 14 for combusting part of the hydrogen generated in the methane reforming part 6.

The operation of the second embodiment shown in FIG. 2 is now described as follows:

The methane.carbon dioxide separation part 4 separates gas containing methane and carbon dioxide, generated by introducing biomass into the anaerobic fermentation part 2, into methane and carbon dioxide. The methane reforming part 6 decomposes the separated methane into carbon and hydrogen. The hydrogen combustion part 14 combusts part of the hydrogen formed in the methane reforming part 6 for generating combustion heat. The reaction in the hydrogen combustion part 14 is as follows:

$$H_2 + (\tfrac{1}{2})O_2 \rightarrow H_2O + 285 \text{ kJ/mol}$$

The remaining part of the hydrogen formed in the methane reforming part 6 is fed to the carbon dioxide fixing part 10, and employed for reducing and fixing the carbon dioxide separated in the methane.carbon dioxide separation part 4.

Figure 3:
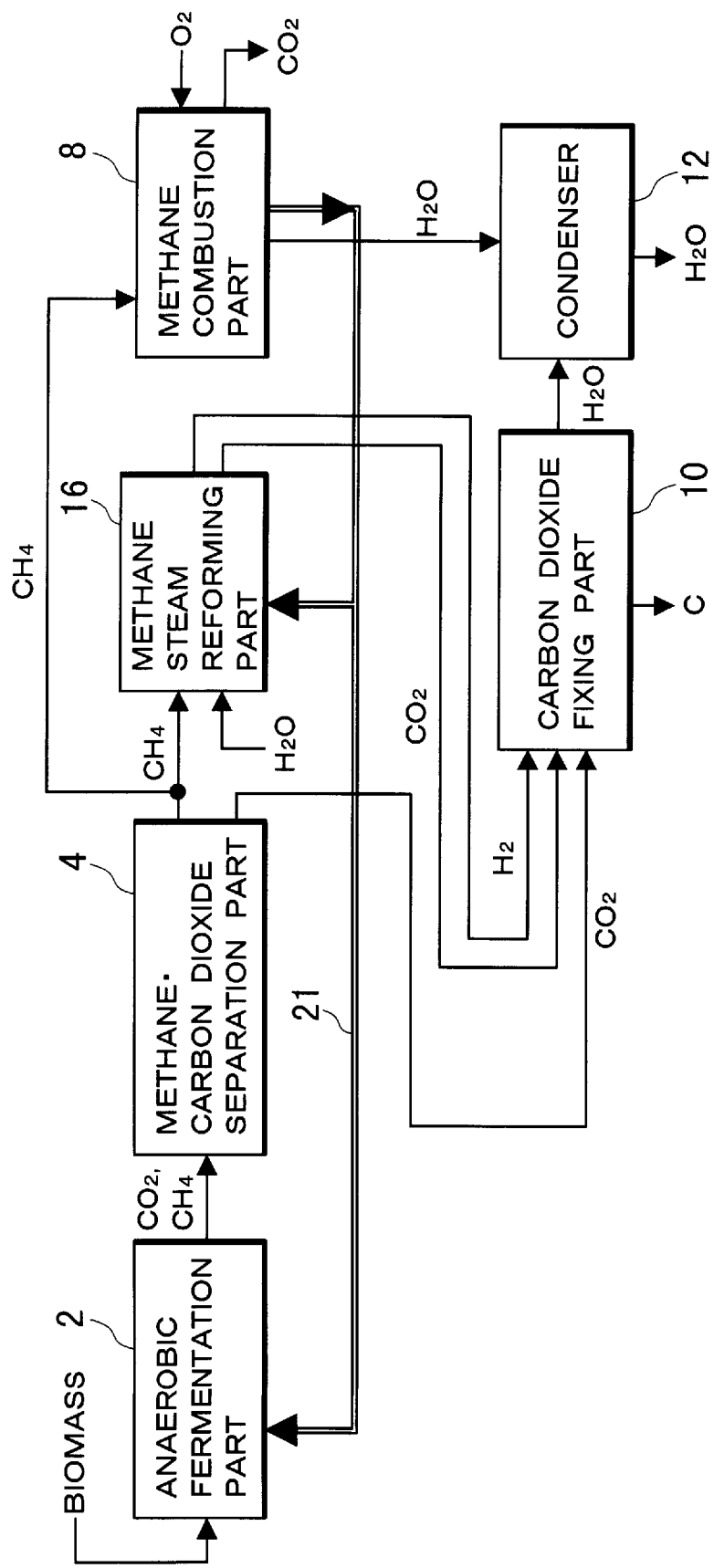
FIG. 3 is a block diagram showing a third embodiment of the present invention.

FIG. 3 is a block diagram showing the third embodiment of the present invention.

Similarly to the first embodiment shown in FIG. 1, the methane.carbon dioxide separation part 4 is connected to the anaerobic fermentation part 2 for separating gas generated in the anaerobic fermentation part 2 into methane and carbon dioxide, while the methane combustion part 8 is provided for combusting part of the methane separated in the methane.carbon dioxide separation part 4 in order to obtain a heat source for the anaerobic fermentation part 2 and the methane reforming part 6.

This embodiment is provided with a methane steam reforming part 16 for forming hydrogen from the methane separated in the methane.carbon dioxide separation part 4, in order to obtain hydrogen for reducing and fixing the carbon dioxide. The methane steam reforming part 16 comprises an Ni catalyst for example, and forms carbon dioxide and hydrogen by reacting methane with steam under the presence of the catalyst under heating at 400 to 900° C. The carbon dioxide fixing part 10 is connected to the methane.carbon dioxide separation part 4 and the methane steam reforming part 16.

The operation of the third embodiment shown in FIG. 3 is now described as follows:

The methane.carbon dioxide separation part 4 separates gas containing methane and carbon dioxide, generated by introducing biomass into the anaerobic fermentation part 2, into methane and carbon dioxide. The methane combustion part 8 combusts part of the separated methane for generating a heat quantity, while the methane steam reforming part 16 reacts the remaining part under the presence of the catalyst for decomposing the same into carbon dioxide and hydrogen. The reaction in the methane steam reforming part 16 is as follows:

$$CH_4 + 2H_2O \rightarrow CO_2 + 4H_2 - 187.4 \text{ kJ/mol}$$

The carbon dioxide fixing part 10 is supplied with the carbon dioxide separated in the methane.carbon dioxide separation part 4 and the hydrogen and carbon dioxide formed in the methane steam reforming part 16 for reducing the carbon dioxide with the hydrogen and fixing the same as pulverized carbon. Carbon dioxide generated in the methane combustion part 8 can also be led to the carbon dioxide fixing part 10 to be fixed as pulverized carbon.

The condensation part 12 condenses and discharges the steam formed in the carbon dioxide fixing part 10 and that formed in the methane combustion part 8.

Figure 4:
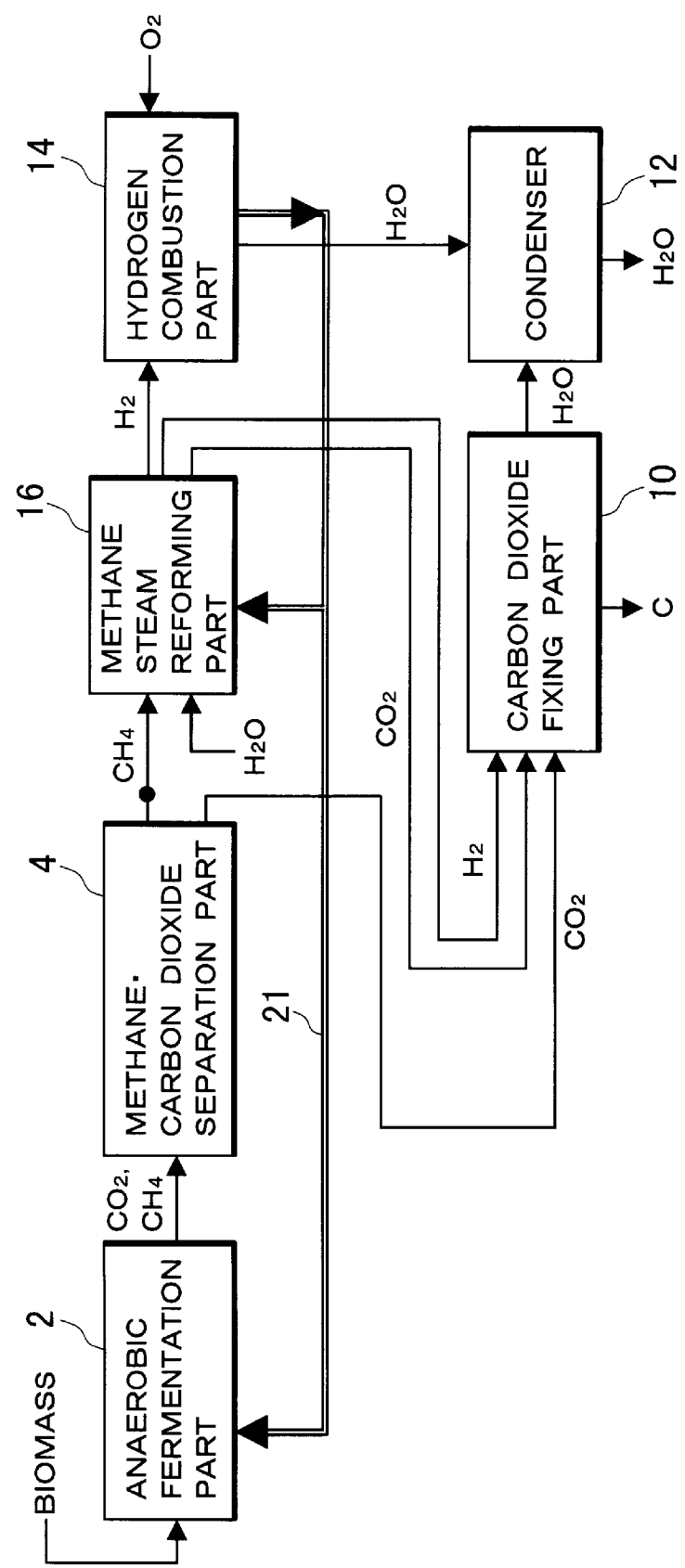
FIG. 4 is a block diagram showing a fourth embodiment of the present invention.

FIG. 4 is a block diagram showing the fourth embodiment of the present invention.

Similarly to the third embodiment shown in FIG. 3, the methane.carbon dioxide separation part 4 is connected to the anaerobic fermentation part 2 for separating gas generated in the anaerobic fermentation part 2 into methane and carbon dioxide, and the methane steam reforming part 16 is provided for forming hydrogen from the methane separated in the methane.carbon dioxide separation part 4 in order to obtain hydrogen for reducing and fixing the carbon dioxide. The carbon dioxide fixing part 10 is connected to the methane.carbon dioxide separation part 4 and the methane steam reforming part 16.

This embodiment is provided with the hydrogen combustion part 14 for combusting part of the hydrogen generated in the methane steam reforming part 16, in order to obtain a heat source for the anaerobic fermentation part 2 and the methane steam reforming part 16.

The operation of the fourth embodiment shown in FIG. 4 is now described as follows:

The methane.carbon dioxide separation part 4 separates gas containing methane and carbon dioxide, generated by introducing biomass into the anaerobic fermentation part 2, into methane and carbon dioxide. The methane steam reforming part 16 decomposes the separated methane into carbon dioxide and hydrogen. The hydrogen combustion part 14 combusts part of the hydrogen formed in the methane steam reforming part 16 for generating combustion heat. The carbon dioxide fixing part 10 is supplied with the carbon dioxide separated in the methane.carbon dioxide separation part 4 and the hydrogen and carbon dioxide formed in the methane steam reforming part 16 for reducing the carbon dioxide with the hydrogen and fixing the same as pulverized carbon.

A condensation part 12 condenses and discharges the steam formed in the carbon dioxide fixing part 10 and that formed in the hydrogen combustion part 14.

Figure 5:
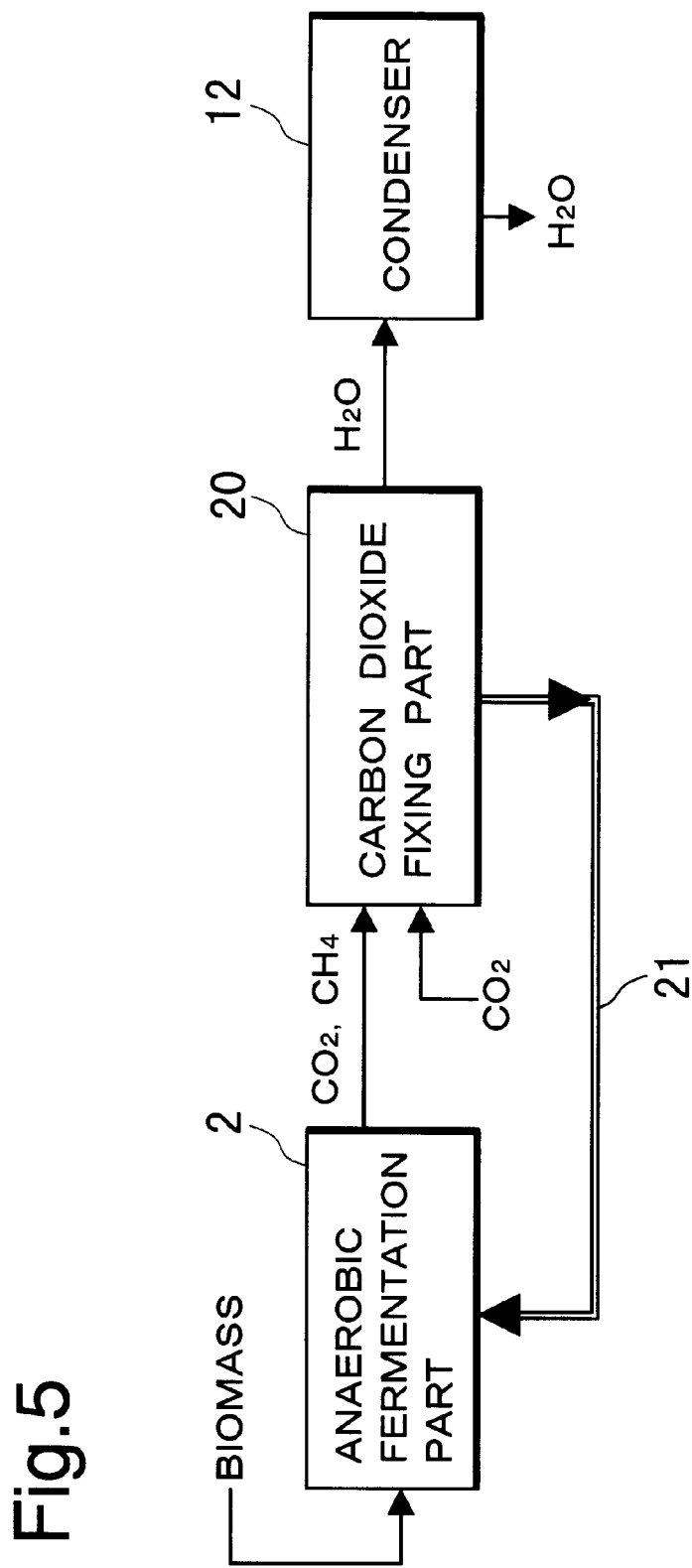
FIG. 5 is a block diagram showing a fifth embodiment of the present invention.

FIG. 5 is a block diagram showing the fifth embodiment of the present invention.

A carbon dioxide fixing part 20 supplied with mixed gas containing methane and carbon dioxide for forming pulverized carbon is connected to the anaerobic fermentation part 2. The carbon dioxide fixing part 20 comprises a catalyst such as Ni or Co with a carrier of $SiO_2$ or $Al_2O_3$ for example, for forming hydrogen by decomposing methane with the catalyst under heating at 400 to 900° C., reducing the carbon dioxide with the formed hydrogen and fixing the same as crystalline pulverized carbon. The carbon dioxide fixing part 20 can be supplied with carbon dioxide from outside the system. A condenser 12 is connected to the carbon dioxide fixing part 20 for condensing and discharging formed steam.

While endothermic and exothermic reactions take place in the carbon dioxide fixing part 20, the reaction heat transmission part 21 is provided similarly to the first embodiment, in order to supply the remaining heat quantity to the anaerobic fermentation part 2 when the quantity of reaction heat resulting from the exothermic reaction is larger than that of the heat consumed by the endothermic reaction.

The operation of the fifth embodiment shown in FIG. 5 is now described as follows:

The ratio of methane to carbon dioxide in the mixed gas generated by introducing biomass into the anaerobic fermentation part 2 is about 7:3. The generated methane and carbon dioxide are supplied to the carbon dioxide fixing part 20 along with carbon dioxide supplied from outside the system.

The carbon dioxide fixing part 20 decomposes the methane into carbon and hydrogen under the presence of a catalyst (methane decomposition step) and reacts the carbon dioxide with the generated hydrogen under the presence of the catalyst for forming carbon and hydrogen (carbon dioxide fixing step). The formed carbon is precipitated as crystalline pulverized carbon in either step. The reactions in the carbon dioxide fixing part 20 are as follows:

Methane decomposition step:

$$CH_4 \rightarrow C+2H_2 - 90.1 \text{ kJ/mol}$$

Carbon dioxide fixing step:

$$CO_2+2H_2 \rightarrow C+2H_2O+96.0 \text{ kJ/mol}$$

The methane decomposition step is an endothermic reaction and the carbon dioxide fixing step is an exothermic reaction. If any heat quantity remains in the carbon dioxide fixing part 20, the heat is utilized as the heat source for the anaerobic fermentation part 2 through the reaction heat transmission part 21.

The ratio of the methane to the carbon dioxide, which are fed from the anaerobic fermentation part 2 to the carbon dioxide fixing part 20, is about 7:3. While the hydrogen formed by decomposing the methane is left after gas supply from the anaerobic fermentation part 2, the formed hydrogen can be entirely consumed by supplying carbon dioxide from outside the system.

Figure 6:
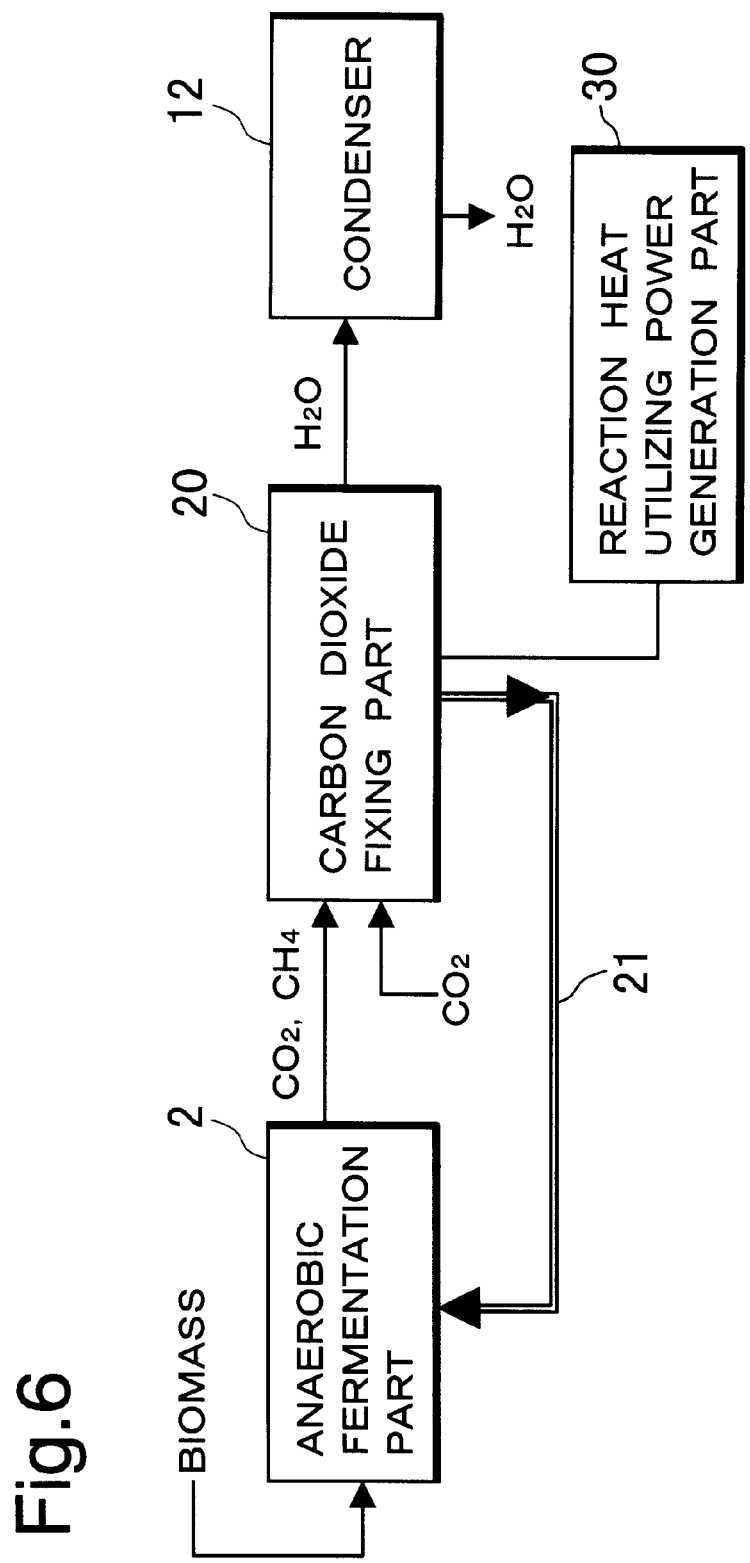
FIG. 6 is a block diagram showing a sixth embodiment of the present invention.

FIG. 6 is a block diagram showing the sixth embodiment of the present invention.

The sixth embodiment is different from the fifth embodiment shown in FIG. 5 in the point that the carbon dioxide fixing part 20 is provided with a reaction heat utilizing power generation part 30. The reaction heat utilizing power generation part 30 converts heat remaining in the carbon dioxide fixing part 20 to electric power for recovering and utilizing the same.

Figure 7:
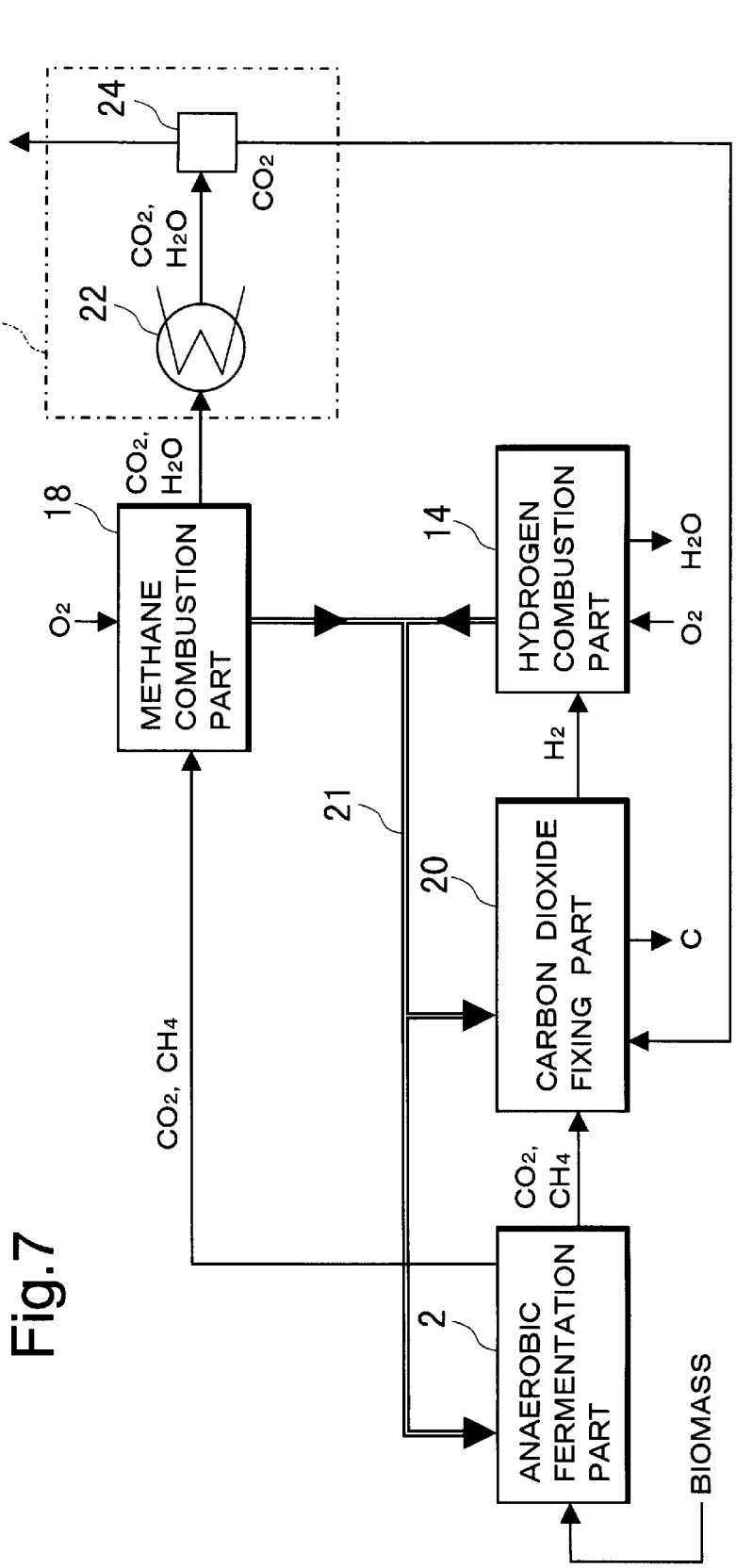
FIG. 7 is a block diagram showing a seventh embodiment of the present invention.

FIG. 7 is a block diagram showing the seventh embodiment of the present invention.

The anaerobic fermentation part 2 is connected to the methane combustion part 18 and the carbon dioxide fixing part 20, for supplying mixed gas containing carbon dioxide and methane thereto.

The methane combustion part 18 combusts the methane and discharges mixed gas containing carbon dioxide and steam. The methane combustion part 18 is connected with an intra-system carbon dioxide supply part 26 formed by a steam condenser 22 and a vapor-liquid separator 24, and a vapor passage from the vaporliquid separator 24 is connected to the carbon dioxide fixing part 20.

The carbon dioxide fixing part 20 is supplied with the mixed gas containing carbon dioxide and methane generated from the anaerobic fermentation part 2 as well as with carbon dioxide from the vapor-liquid separator 24, with no supply of carbon dioxide from outside the system. Therefore, the quantity of hydrogen generated through the methane decomposition step in the carbon dioxide fixing part 20 exceeds that consumed in the carbon dioxide fixing step. In order to combust the residual hydrogen, the hydrogen combustion part 14 is connected to the carbon dioxide fixing part 20. The carbon dioxide fixing part 20, predominantly causing an endothermic reaction (methane decomposition step) in quantity as compared with an exothennic reaction (carbon dioxide fixing step), requires external energy as a whole. In order to supplement the energy, combustion heat obtained in the hydrogen combustion part 14 and the methane combustion part 18 is supplied to the anaerobic fermentation part 2 and the carbon dioxide fixing part 20 through a reaction heat transmission part 21.

The operation of the seventh embodiment shown in FIG. 7 is now described as follows:

Part of mixed gas containing methane and carbon dioxide generated by introducing biomass into the anaerobic fermentation part 2 is fed to the carbon dioxide fixing part 20, which in turn forms carbon and hydrogen through the methane decomposition step and reduces the carbon dioxide with the hydrogen and fixes the same in the carbon dioxide fixing step. The ratio of the methane to the carbon dioxide fed from the anaerobic fermentation part 2 to the carbon dioxide fixing part 20 is about 7:3, and the hydrogen formed by decomposing the methane is left after reaction with the carbon dioxide even with addition of carbon dioxide supplied from the vapor-liquid separator 24.

The residual hydrogen is fed to the hydrogen combustion part 14, which in turn combusts the same.

Part of the mixed gas containing methane and carbon dioxide generated in the anaerobic fermentation part 2 is also fed to the methane combustion part 18, which in turn combusts the methane for generating a heat quantity.

Carbon dioxide and steam formed in the methane combustion part 18 are fed to the steam condenser 22 to be condensed and thereafter separated into carbon dioxide and water by the vapor-liquid separator 24. All carbon dioxide formed in the system of the apparatus can be fixed by feeding the separated carbon dioxide by the vapor-liquid separator 24 to the carbon dioxide fixing part 20.

Figure 8:
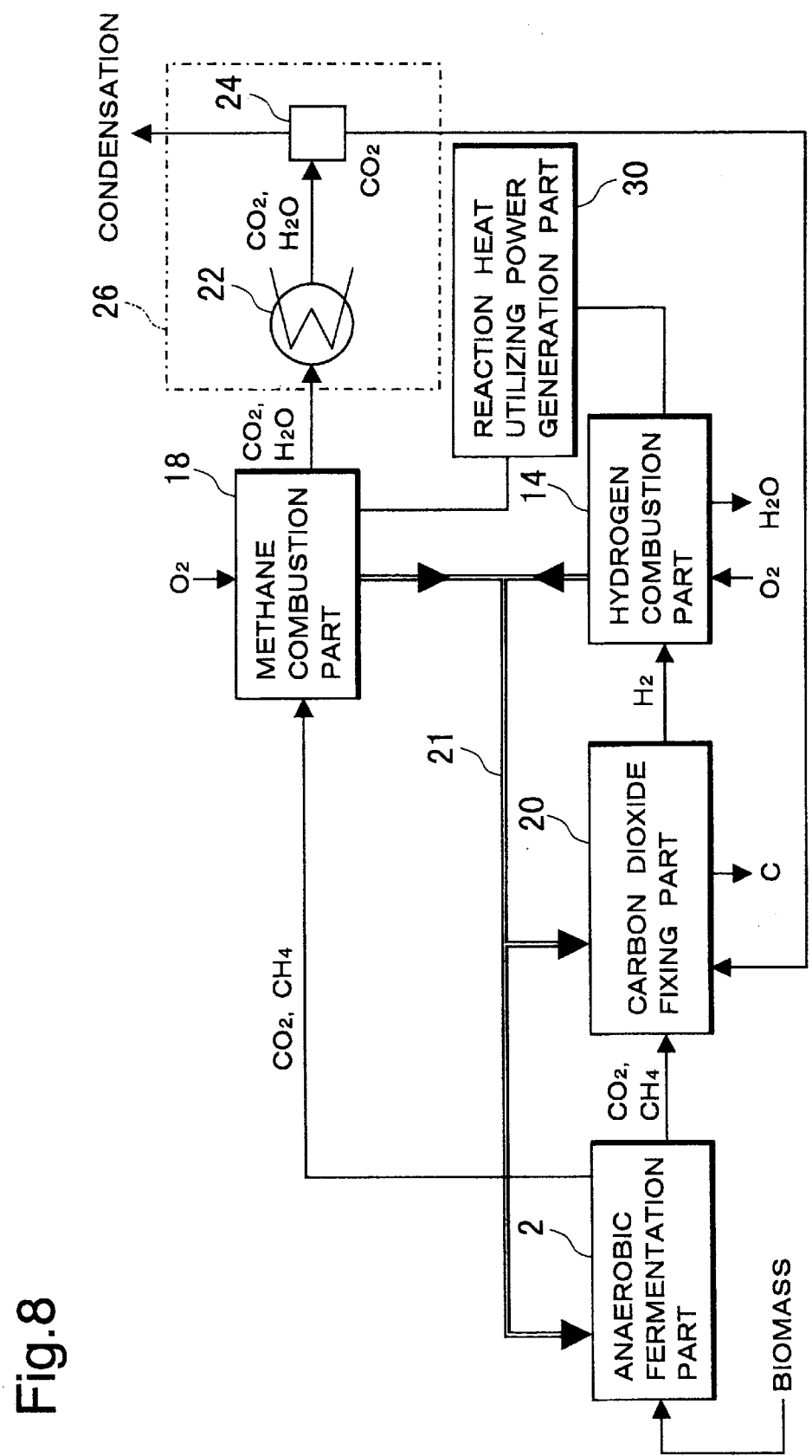
FIG. 8 is a block diagram showing an eighth embodiment of the present invention.

FIG. 8 is a block diagram showing the eighth embodiment of the present invention.

The eighth embodiment is different from the seventh embodiment shown in FIG. 7 in the point that the reaction heat utilizing power generation part 30 is provided for a hydrogen combustion part 14 and a methane combustion part 18.

By providing the reaction heat utilizing power generation part 30, heat left in the hydrogen combustion part 14 or the methane combustion part 18 can be converted to electric power to be recovered and utilized.

FIG. 9 is a block diagram showing the ninth embodiment of the present invention.

The anaerobic fermentation part 2 is connected with the methane combustion part 18 and the carbon dioxide fixing part 20, for supplying mixed gas containing methane and carbon dioxide generated therein to the methane combustion part 18 and the carbon dioxide fixing part 20 respectively. Mixed gas containing carbon dioxide and steam generated in the methane combustion part 18 by combusting the methane is fed to the carbon dioxide fixing part 20 through a passage. The reaction heat transmission part 21 is provided for supplying combustion heat obtained in the methane combustion part 18 to the anaerobic fermentation part 2.

The operation of the ninth embodiment shown in FIG. 9 is now described as follows:

Part of mixed gas containing methane and carbon dioxide, generated by introducing biomass into the anaerobic fermentation part 2, is fed to the carbon dioxide fixing part 20, which in turn reacts the methane and the carbon dioxide under the presence of a catalyst for forming crystalline pulverized carbon and steam.

The remaining part of the mixed gas containing methane and carbon dioxide generated in the anaerobic fermentation part 2 is fed to the methane combustion part 18, which in turn combusts the methane. The reaction heat transmission part 21 supplies combustion heat obtained in the methane combustion part 18 to the anaerobic fermentation part 2, for utilizing the same as the heat source for the anaerobic fermentation part 2.

Carbon dioxide and steam formed in the methane combustion part 18 are fed to the carbon dioxide fixing part 20. The ratio of the methane to the carbon dioxide generated in the anaerobic fermentation part 2 is about 7:3, and hence the methane is left in the carbon dioxide fixing part 20 reacting the methane and the carbon dioxide in the ratio of 1:1. All carbon dioxide formed in the system of the apparatus can be fixed by adjusting the ratio of the gas, generated in the anaerobic fermentation part 2, fed to the carbon dioxide fixing part 20 to that fed to the methane combustion part 18 so that the sum of the mole numbers of the carbon dioxide fed from the methane combustion part 18 to the carbon dioxide fixing part 20 and that fed from the anaerobic fermentation part 2 to the carbon dioxide fixing part 20 is equal to the mole number of the methane fed to the carbon dioxide fixing part 20.

FIG. 10 is a block diagram showing the tenth embodiment of the present invention.

The tenth embodiment is different from the ninth embodiment shown in FIG. 9 in the point that the reaction heat utilizing power generation part 30 is provided for a methane combustion part 18.

By providing the reaction heat utilizing power generation part 30, heat left in the methane combustion part 18 can be converted to electric power to be recovered and utilized.

The embodiments shown in FIGS. 1 to 10 can fix carbon dioxide, which is greenhouse effect gas causing the global anathermal, and hence can contribute to the global environment The pulverized carbon obtained in the methane reforming part 6 or the carbon dioxide fixing part 10 or 20 can substitute for industrial carbon black Thus, that generally prepared from fossil material can be converted to that prepared from biomass, for contributing to the saving of resources. Part of the obtained carbon may contain value-added fullerene or carbon nanotube, and can be utilized as a byproduct through purification.

When leading the combustion heat generated in the methane combustion part 8 or 18 or the hydrogen combustion part 14 to the anaerobic fermentation part 2, the methane reforming part 6 or the methane steam reforming part 16, energy for heating an anaerobic fermenter of the anaerobic fermentation part 2 for prompting fermentation of the biomass can be reduced, heat for the endothermic reaction in the methane reforming part 6 or the methane steam reforming part 16 can be supplemented, and the cost can be reduced.

When heat is excessively generated in the carbon dioxide fixing part 20, the excess heat can also be utilized for heating the remaining parts, thereby contributing to cost reduction.

When comprising the reaction heat utilizing power generation part for converting the heat generated in the methane combustion part 8 or 18, the hydrogen combustion part 14 or another part to electric power, part of the electric power for operating the apparatus can be provided for reducing the cost. A gas turbine or the like can be connected to the methane combustion part 8 or 18, the hydrogen combustion part 14 or another heat generating part for utilizing waste heat While the carbon dioxide used in the carbon dioxide fixing part 10 or 20 is mainly supplied from the anaerobic fermentation part 2, the methane.carbon dioxide separation part 4 or the methane steam reforming part 16, all carbon dioxide generated in the system of the apparatus can be fixed by also leading and fixing the carbon dioxide generated in the methane combustion part 8 or 18 or the hydrogen combustion part 14.

Although the present invention has been described and illustrated in detail, it is clearly understood that the same is by way of illustration and example only and is not to be taken by way of limitation as the spirit and scope of the present invention is limited only by the terms of the appended claims.

We claim:

1. A carbon producing apparatus comprising:
    an anaerobic fermentation part for generating methane and carbon dioxide by anaerobically fermenting biomass;
    a methane.carbon dioxide separation part for separating methane and carbon dioxide, supplied with mixed gas containing methane and carbon dioxide generated in said anaerobic fermentation part;
    hydrogen forming means for forming hydrogen, supplied with methane separated in said methane.carbon dioxide separation part; and
    a carbon dioxide fixing part for forming carbon by reducing carbon dioxide with hydrogen under the presence of a catalyst, supplied with carbon dioxide separated in said methane.carbon dioxide separation part and with hydrogen formed in said hydrogen forming means.

2. The carbon producing apparatus in accordance with claim 1, wherein
    said hydrogen forming means is a methane reforming part for decomposing methane into carbon and hydrogen under the presence of a catalyst.

3. The carbon producing apparatus in accordance with claim 1, wherein
    said hydrogen forming means is a methane steam reforming part for forming carbon dioxide and hydrogen by reacting methane with steam under the presence of a catalyst.

4. The carbon producing apparatus in accordance with claim 1, further comprising a methane combustion part supplied with part of said methane separated in said methane.carbon dioxide separation part and a reaction heat transmission part for supplying heat generated in said methane combustion part to said anaerobic fermentation part and said hydrogen forming means.

5. The carbon producing apparatus in accordance with claim 4, further comprising a reaction heat utilizing power generation part supplied with said heat generated in said methane combustion part, for converting said part of said heat generated in said methane combustion part to electric power.

6. The carbon producing apparatus in accordance with claim 4, providing a passage supplying gas containing carbon dioxide generated from said methane combustion part to said carbon dioxide fixing part, for also reducing said carbon dioxide contained in said gas to carbon.

7. The carbon producing apparatus in accordance with claim 4, further providing an intra-system carbon dioxide supply part formed by a steam condenser and a vapor-liquid separator supplied with mixed gas containing steam and carbon dioxide generated from said methane combustion part and a passage supplying said carbon dioxide separated in said vapor-liquid separator to said carbon dioxide fixing part, for also reducing said carbon dioxide to carbon.

8. The carbon producing apparatus in accordance with claim 1, further comprising a hydrogen combustion part supplied with part of said hydrogen formed in said hydrogen forming means and a reaction heat transmission part for supplying heat generated in said hydrogen combustion part to said anaerobic fermentation part and said hydrogen forming means.

9. The carbon producing apparatus in accordance with claim 8, further comprising a reaction heat utilizing power generation part supplied with said heat generated in said hydrogen combustion part, for converting said part of said heat generated in said hydrogen combustion part to electric power.

10. A carbon producing apparatus comprising:

an anaerobic fermentation part for generating methane and carbon dioxide by anaerobically fermenting biomass; and a carbon dioxide fixing part supplied with mixed gas containing methane and carbon dioxide formed in said anaerobic fermentation part for generating carbon by reacting the same under the presence of a catalyst.

11. The carbon producing apparatus in accordance with claim 10, wherein said carbon dioxide fixing part is also supplied with carbon dioxide from outside the system.

12. The carbon producing apparatus in accordance with claim 10, further comprising a methane combustion part supplied with part of said mixed gas containing methane and carbon dioxide formed in said anaerobic fermentation part for combusting said methane contained in said mixed gas and a reaction heat transmission part for supplying heat generated in said methane combustion part to said anaerobic fermentation part.

13. The carbon producing apparatus in accordance with claim 12, further comprising a reaction heat utilizing power generation part supplied with part of said heat generated in said methane combustion part, for converting said part of said heat generated in said methane combustion part to electric power.

14. The carbon producing apparatus in accordance with claim 12, providing a passage supplying gas containing carbon dioxide generated from said methane combustion part to said carbon dioxide fixing part, for also reducing said carbon dioxide contained in said gas to carbon.

15. The carbon producing apparatus in accordance with claim 14, wherein the ratio of gas, generated in said anaerobic fermentation part, fed to said carbon dioxide fixing part to that fed to said methane combustion part is so adjusted that the sum of the mole numbers of said carbon dioxide fed from said methane combustion part to said carbon dioxide fixing part and that fed from said anaerobic fermentation part to said carbon dioxide fixing part is equal to the mole number of said methane fed to said carbon dioxide fixing part.

16. The carbon producing apparatus in accordance with claim 12, further providing an intra-system carbon dioxide supply part formed by a steam condenser and a vapor-liquid separator supplied with mixed gas containing steam and carbon dioxide generated from said methane combustion part and a passage supplying carbon dioxide separated in said vapor-liquid separator to said carbon dioxide fixing part, for also reducing said carbon dioxide to carbon.

17. The carbon producing apparatus in accordance with claim 12, wherein the ratio of gas, generated in said anaerobic fermentation part, fed to said carbon dioxide fixing part to that fed to said methane combustion part is so adjusted that the sum of the mole numbers of said carbon dioxide fed from said methane combustion part to said carbon dioxide fixing part and that fed from said anaerobic fermentation part to said carbon dioxide fixing part is equal to the mole number of said methane fed to said carbon dioxide fixing part.

18. The carbon producing apparatus in accordance with claim 10, further comprising a hydrogen combustion part supplied with hydrogen formed in said carbon dioxide fixing part and a reaction heat transmission part for supplying heat generated in said hydrogen combustion part to said anaerobic fermentation part.

19. The carbon producing apparatus in accordance with claim 18, further comprising a reaction heat utilizing power generation part supplied with part of said heat generated in said hydrogen combustion part for converting said part of said heat generated in said hydrogen combustion part to electric power.

\* \* \* \* \*